United States Patent [19]
Kobayashi et al.

[11] Patent Number: 6,110,688
[45] Date of Patent: Aug. 29, 2000

[54] PROCESS FOR PURIFYING TAMM-HORSFALL GLYCOPROTEIN OR UROMODULIN THEIR PURIFIED PRODUCTS AND METHOD FOR MAKING THE DISCRIMINATION BETWEEN BOTH OF THEM

[75] Inventors: Hideyuki Kobayashi, Kobe; Yoshikazu Komurasaki, Miki; Keihide Koh; Satoshi Nishimuro, both of Kobe, all of Japan

[73] Assignee: JCR Pharmaceuticals Co., Ltd., Hyogo, Japan

[21] Appl. No.: 08/766,742

[22] Filed: Dec. 13, 1996

[30] Foreign Application Priority Data

Dec. 14, 1995 [JP] Japan .................................. 7-347939

[51] Int. Cl.[7] ............................. C07K 14/47; C07K 16/18
[52] U.S. Cl. ........................... 435/7.1; 435/7.9; 435/7.92; 436/177; 436/814; 210/645; 530/350
[58] Field of Search ............................ 530/350; 436/177, 436/814; 435/7.1, 7.9, 7.92; 210/645

[56] References Cited

U.S. PATENT DOCUMENTS 4,977,244  12/1990  Muchmore .
5,667,979   9/1997  Berrens .

FOREIGN PATENT DOCUMENTS

WO 87 00183  1/1987  WIPO .

OTHER PUBLICATIONS

*The Merck Index*, 10th Ed. Windholz M., Ed., Merck & Co., Inc. Rathway, NJ, USA, 1983, p4856.

Hunt et al. Biochem J. vol. 227, 1985, p957–963.

Kjellsson et al. J. Immunol Meth, vol. 98, 1987, p 105–111.

Yanagisawa et al. J Lipid Res. 25(7). 1984. p 750–753.

Moonen et al., *FEBS Letters*, "Native cytokines do not bind to uromodulin (Tamm–Horsfall glycoprotein", vol. 226, No. 2, Jan. 1988.

Muchmore et al., *Science*, "Uromodulin: a Unique 85–Kilo-dalton Immunosuppressive Glycoprotein Isolated from Urine of Pregnant Women", vol. 229, Aug. 2, 1985.

Adlington et al., *Bioorganic & Medicinal Chemistry Letters*, "Design and synthesis of novel monocyclic beta–lactam inhibitors of prostate specific antigen", vol. 7, No. 13, Jul. 8, 1997.

Cohen et al., *Journal of Clinical Endocrinology and Metabolism*, "Prostate–specific Antigen (PSA) is an Insulin–like Growth Factor Binding Protein–3 Protease Found in Seminal Plasma", vol. 75, No. 4, Oct. 1992.

Leinonen et al., *Jounral of Urology*, "Complex Formation Between PSA Isoenzymes and Protease Inhibitors", vol. 155, No. 3, Mar. 1996.

Fielder, *Growth Regulation*, "Biochemical analysis of PSA–proteolyzed IGFBP–3", vol. 4, No. 4, Dec. 1994.

*Primary Examiner*—Phuong T. Bui
*Attorney, Agent, or Firm*—Jacobson, Price, Holman & Stern, PLLC

[57] ABSTRACT

The present invention provides a process for purifying Tamm-Horsfall glycoprotein (THG) and uromodulin, which permits THG and uromodulin to be purified with enhanced efficiency by the simplified procedure, as well as a method for making the discrimination between both of them.

6 Claims, 5 Drawing Sheets

An elution pattern obtained when a purified specimen originated from male urine was subjected to gel permeation with use of HPLC. The arrow symbol designates a THG fraction.

Electrophoretic patterns obtained when a THG fraction was subjected to SDS-PAGE under the reducing (Lanes 1 and 2) and non-reducing conditions (Lanes 3 and 4).

Notes: Lanes 1 and 3; M.W. marker
Lanes 2 and 4; THG specimen

An elution pattern obtained when a purified specimen originated from pregnancy urine was subjected to gel permeation with use of HPLC. The arrow symbol designates a uromodulin fraction.

Electrophoretic patterns obtained when a uromodulin fraction was subjected to SDS-PAGE under the reducing (Lanes 1 and 2) and non-reducing conditions (Lanes 3 and 4).

Notes: Lanes 1 and 3; M.W. marker
Lanes 2 and 4; THG specimen (a) Affinities of THG and uromodulin for human IgG (b) Affinities of THG and uromodulin for human IgG F(ab')$_2$ Notes:
The symbols "○" and "●" designate THG and uromodulin, respectively.

PROCESS FOR PURIFYING TAMM-HORSFALL GLYCOPROTEIN OR UROMODULIN THEIR PURIFIED PRODUCTS AND METHOD FOR MAKING THE DISCRIMINATION BETWEEN BOTH OF THEM

The present invention relates to a process for purifying Tamm-Horsfall glycoprotein (hereinafter referred to briefly as "THG"), or uromodulin, which is of a human urine origin, to their purified products and to a method for making the discrimination between both of such proteins with use of immunoglobulins.

BACKGROUND OF THE INVENTION

THG was initially discovered as a urinary mucoprotein (Morner Kah, 1895, Skand. Arch. Physiol. 6:332) and was thereafter reported to be a factor acting to inhibit in urine viral hemagglutination (Tamm, I. and Horsfall, E. L., 1950, Proc. Soc. Exp. Biol. Med., 74: 108). Referring specifically to the purification process for THG, a pool of urine collected is stored at 4° C. overnight, and the resultant supernatant as separated out, after a portion of the same is discarded, is admixed with sodium chloride to a concentration of 0.58 M, followed by stirring and centrifugation; the resultant precipitate is collected and dissolved in water, followed by centrifugation, and the supernatant is collected and freeze-dried to thereby give a lyophilisate, which is regarded as THG. Subsequently, THG has been purified by means of a variety of the modified processes devised by a large number of researchers, whereby purification is fundamentally effected along the line of the above-described procedure (Moonen, P. et al., FEBS Lett., 226:314. Toma, G. et al., 1994, Biochem. Biophys. Res. Commun., 200: 275).

On the other hand, uromodulin, a glycoprotein showing the same amino acid sequence as THG, was purified from urine of pregnant women (Muchmore, A. V. and Decker, J. M., 1985, Science, 229:479). Pregnancy urine was subjected to a lectin column (Con A-Sepharose column), and after elution with α-methylmannose, the eluate was dialyzed against water, followed by lyophilization; the lyophilizate was then dissolved in phosphate buffer saline, and the solution was subjected to separation by isoelectric focusing, followed by concentration through ultrafiltration membranes to thereby purify uromodulin. Uromodulin, whose carbohydrate chain or moiety elicits numerous functions, has been considered to be a specific ligand for cytokines, such as IL-1, IL-2 and tumor necrosis factor (TNF) (Hession, C., et al., 1987, Science, 237: 1497. Sherblom, A. P., et al., 1989, J. Immunol., 143: 939, Brown, K. M., et al., 1986, Proc. Natl. Acad. Sci. U.S.A., 83: 9119, and Winkelstein, A., et al., 1990, Immunopharmacology, 20: 201). In recent years, however, what is purified from urine merely by the salting out method is referred to as "THG", and what is purified from pregnancy urine by the salting out method is called "uromodulin".

THG contains carbohydrates in quantity equivalent to about 30% of the molecular weight and possesses a carbohydrate chain structure being rich in mannose represented by $GluNa_2$ and Man (5–7) wherein GluNa and Man denote N-acetylglucosamine and mannose, respectively. And it has been proven that the carbohydrate residues of Man 5 and Man 6 bind specifically to cytokines, inclusive of IL-1, IL-2 and tumor necrosis factor (TNF). These findings suggest the possibility that THG would be involved in the immunomodulatory mechanism, and at the same time, uromodulin showing the same amino acid sequence as THG was reported to exhibit immunosuppressive activity greater than 10 times more potent than THG. Also a report was recently published that THG of a sheep origin binds to sheep's IgG, while THG of a human origin likewise binds to human IgG (Rhodes, D. C. J. et al., 1993, Kidney Int., 44: 1014). Consequently, THG is considered to play a key role in novel immunomodulation or immune protection in the renal tubules, in addition to the immunoregulation mechanism mediated through cytokines.

In purifying THG and uromodulin, many researchers employ the above-mentioned salting out method. Nevertheless, the method incurs the risk of allowing not only the objective protein but also many other impurities to precipitate in entanglement with the protein, and this requires additional steps of removing such impurities to be provided in the subsequent purification procedure. In order to overcome such disadvantage, the objective protein must be precipitated under milder operating conditions. Furthermore, THG and uromodulin tend to gel readily in solution when such metal ions as $Na^+$ and $Ca^{++}$, coexist, and it is therefore far from being easy to dissolve the lyophilized THG in isotonic saline. For the reason of this, it is desirable to conduct purification of THG under physiological conditions from the beginning without incorporating the step of lyophilization in the purification process. Moreover, if THG and uromodulin individually are able to be assayed accurately and methods for quantitatively determining each of them are established accordingly, these would be considered to serve a useful purpose to clarify more efficiently their physiological and clinical significances.

The present inventors found that urine, whether it is ordinary urine or pregnancy urine, upon freezing and thawing, yields precipitates in large volume in which a great deal of THG is contained, and succeeded in allowing THG to precipitate in great quantities in one step of freezing and thawing without resorting to the salting out method. In contrast to the salting out method, moreover, the novel process does not cause rapid precipitation and was found to offer the advantage that impurities are less susceptible to entanglement in the precipitate. On the basis of simplification of the purification process by eliminating a number of steps required for the conventional counterparts, furthermore, the present inventors discovered that gel permeation by use of high performance liquid chromatography (hereinafter referred to briefly as "HPLC") can remove efficiently impurities (composed mainly of coloring matters), while the collected fraction containing the objective protein, after passing through, for example, a filter of about 0.2 μm in pore size, can be stored at a temperature of 4° C. without being freeze-dried. Referring to uromodulin, the inventors have established a process which enables the same to be purified from pregnancy urine by means of the benzoate precipitation method in addition to the above-described freezing-thawing precipitation method. It was also found that the purified THG binds to the human immunoglobulin classes of IgG, IgA and Ig M and all of the IgG subclasses of IgG1, IgG2, IgG3 and IgG4 as well as the F(ab')$_2$ fragment of IgG, whereas the purified uromodulin binds to the human immunoglobulin classes of IgG and IgA and the IgG subclasses of IgG1, IgG2 and IgG4, though it does not bind readily to IgM, the IgG subclass of IgG3 and the F(ab')$_2$ fragment of IgG.

SUMMARY OF THE INVENTION

The present invention has been completed based on these findings, and relates to a process for purifying THG or uromodulin, which comprises freezing human urine, followed by thawing to thereby collect the resultant precipitate fraction, or adding sodium or ammonium benzoate to human urine and then making the solution acid enough to allow benzoic acid to crystallize out to thereby collect the resultant precipitate fraction, to the purified THG or uromodulin each showing the characteristic properties, and to a method for making the discrimination between THG and uromodulin, which comprises acting on a specimen an immunoglobulin being less capable of binding readily to uromodulin, such as F(ab') fragment of IgG, and assaying the acted amount of the immunoglobulin.

DETAILED DESCRIPTION

Freezing and thawing or unfreezing of human urine can be carried out by the conventionally known procedures, whereby the precipitate fraction formed in the thawed solution is collected. It suffices to add sodium or ammonium benzoate to human urine at a ratio of about 2% (W/V), and the resultant solution, upon addition of e.g. hydrochloric acid to turn to the acid range of pH 3 to 4, deposits benzoic acid, wherein the deposited benzoic acid adsorbs the desired protein and sediments. The precipitate fraction is separated out and admixed with ethanol, followed by stirring to thereby give a precipitate freed of benzoic acid through dissolution in ethanol.

The precipitate fraction obtained by the above-described procedure can be further purified, for example, by dissolving the same in phosphate buffer saline, followed by gel permeation to remove impurities including coloring matters, etc.

The purified product obtained in this manner, when it is the purified THG, shows the characteristic property that it binds to IgG through its $F(ab')_2$ fragment, IgA (monomer) and IgM, which are the immunoglobulin classes, and all of IgG1, IgG2, IgG3 and IgG4, which are the IgG subclasses, and when it is the purified uromodulin, exhibits on the other hand the characteristic property that it binds to IgG and IgA (monomer) which are the human immunoglobulin classes and IgG1, IgG2 and IgG4 which are the IgG subclasses, whereas it does not bind readily to IgG through its $(F(ab')_2$ fragment and IgM which are the human immunoglobulin classes and Ig3 which is the IgG subclass.

Such being the case, the discrimination can be made between THG and uromodulin by immobilizing the purified product by the known means, followed by action of the human immunoglobulin class of IgM or the IgG subclass of IgG3, and then assaying the acted amount of either of the immunoglobulins with an enzyme-labeled protein C or by acting directly the $F(ab')_2$ fragment of enzyme-labeled IgG on the purified product and then assaying the acted amount of the same.

Endotoxin shock and sepsis are considered to be caused by cytokines IL-1 and TNF being involved in the inflammation, while THG or uromodulin originated from human urine exhibits inhibitory activity against cytokine IL-1, and consequently THG and uromodulin are effective as a therapeutic agent against such diseases. Also, THG and uromodulin, with their reactivities toward the immunoglobulins, are thought to possess infection-resistance potentiating activity. Since there has been established an immunoglobulin-based method for making the discrimination between THG and uromodulin, in addition, the present invention is useful in elucidating the physiological and clinical significances of these proteins.

According to the present invention, THG and uromodulin can be purified with enhanced efficiency by the simplified procedure to thereby produce the purified products exhibiting their characteristic properties, and by taking full advantage of such characteristic properties, the discrimination can be made between THG and uromodulin.

BRIEF DESCRIPTION OF THE DRAWINGS

Described below are the examples to illustrate this invention in more detail, but this invention is not intended to be limited by these examples, wherein in the attached sheets:

FIG. 5A and FIG. 5B shows graphs illustrating progresses of the reactions of THG and uromodulin immobilized on the microplate with human immunoglobulin or the $F(ab')_2$ fragment of IgG, as conducted in Examples 3 and 4, demonstrating that THG and uromodulin each can be distinguished and discriminated from the other on the basis of differences in affinity for the $F(ab')_2$ fragment of human IgG.

EXAMPLE 1

Figure 1:
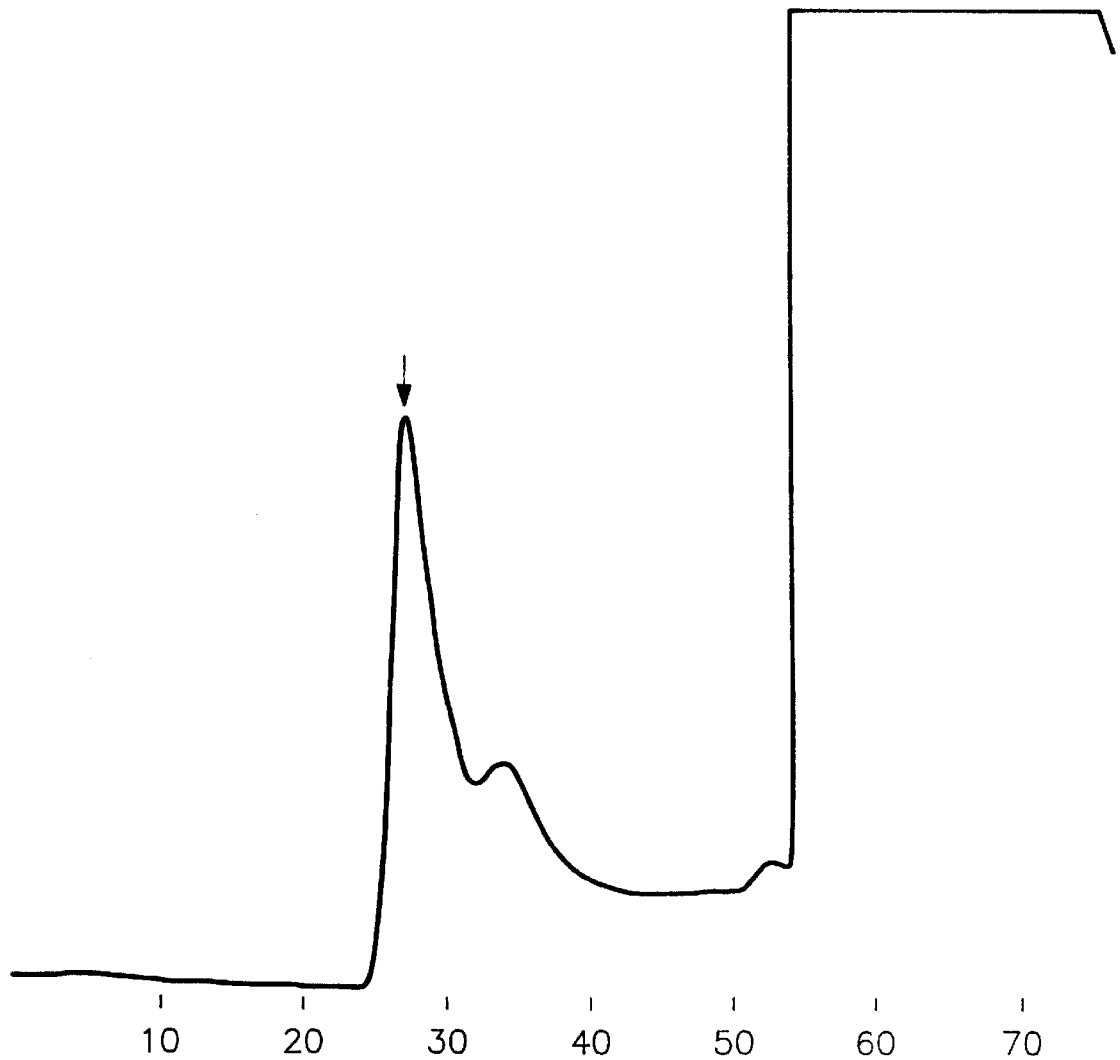
FIG. 1 is an elution pattern obtained when a specimen prepared in Example 1 by purifying human urine by the freezing-thawing process was subjected to gel filtration.
Figure 2:
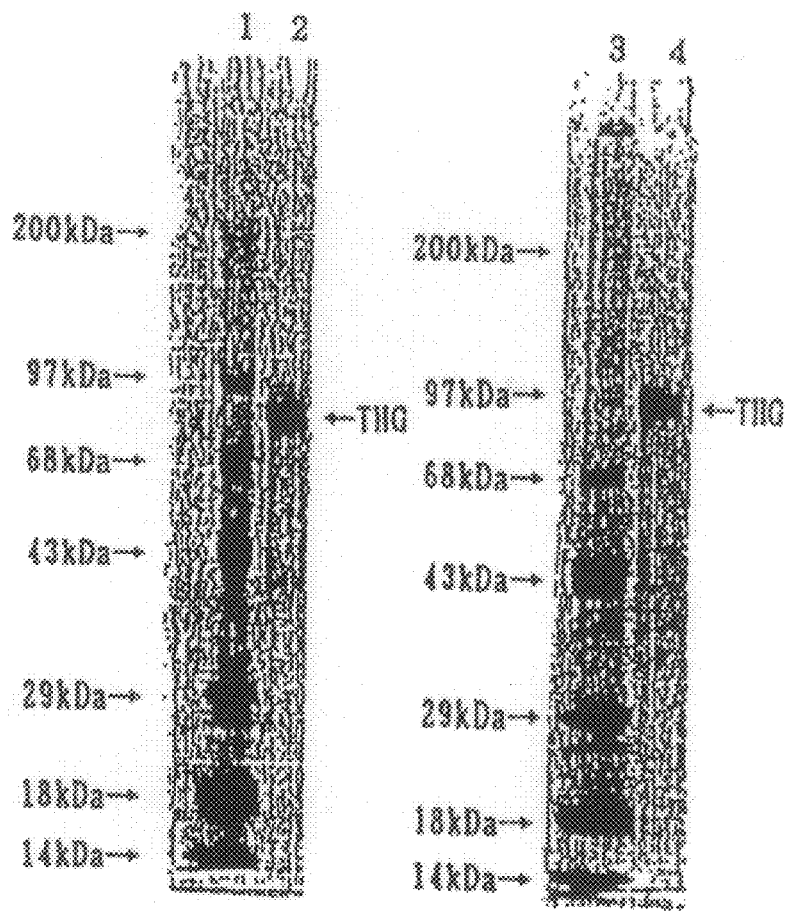
FIG. 2 is a photograph showing the electrophoretic patterns obtained when THG as purified in Example 1 was subjected to SDS-PAGE individually under the reducing and non-reducing conditions.

Normal human urine was pooled, frozen at −20° C. and then thawed at 4° C. to thereby give a precipitate. The precipitate separated out was centrifuged at 3,000× g for 30 min, and the supernatant was discarded, while the precipitate was dissolved in phosphate buffer saline (PBS), followed by dialysis against PBS and centrifugation. The resultant supernatant was separated and concentrated by Amicon, and the concentrate was subjected to HPLC, followed by gel permeation of the mobile phase under the PBS condition (TSK-300SW: manufactured by Tosoh Inc. of Japan) (see FIG. 1). A fraction being eluted in the void volume was subjected to SDS-PAGE to identify the molecular weight and degree of purity (see FIG. 2). Urine of pregnant women (in the second and a half month to sixth month of pregnancy) was also able to be purified by the above-mentioned procedure.

EXAMPLE 2

Figure 3:
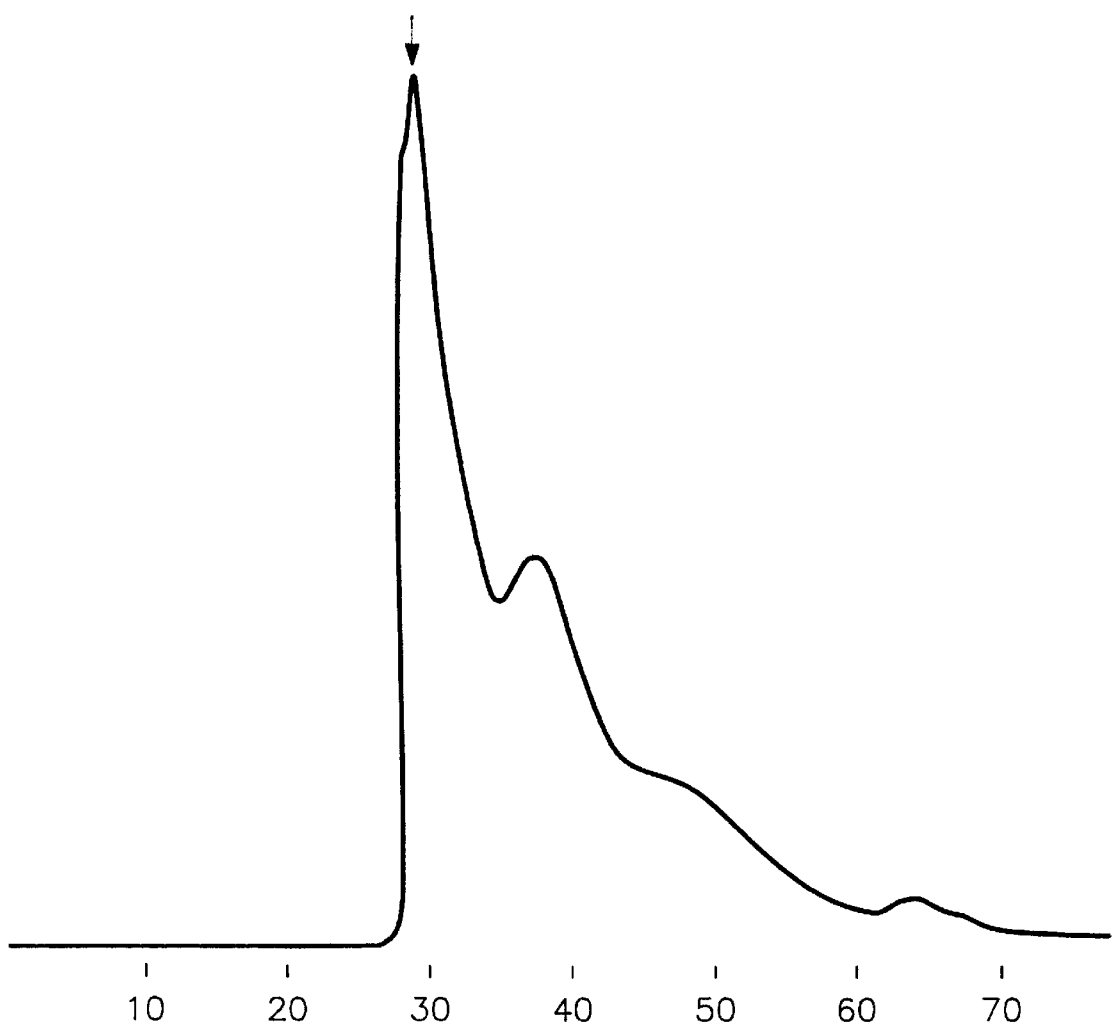
FIG. 3 is an elution pattern obtained when a specimen prepared by purifying pregnancy urine of by the benzoate-adsorption precipitation process was subjected to gel permeation.
Figure 4:
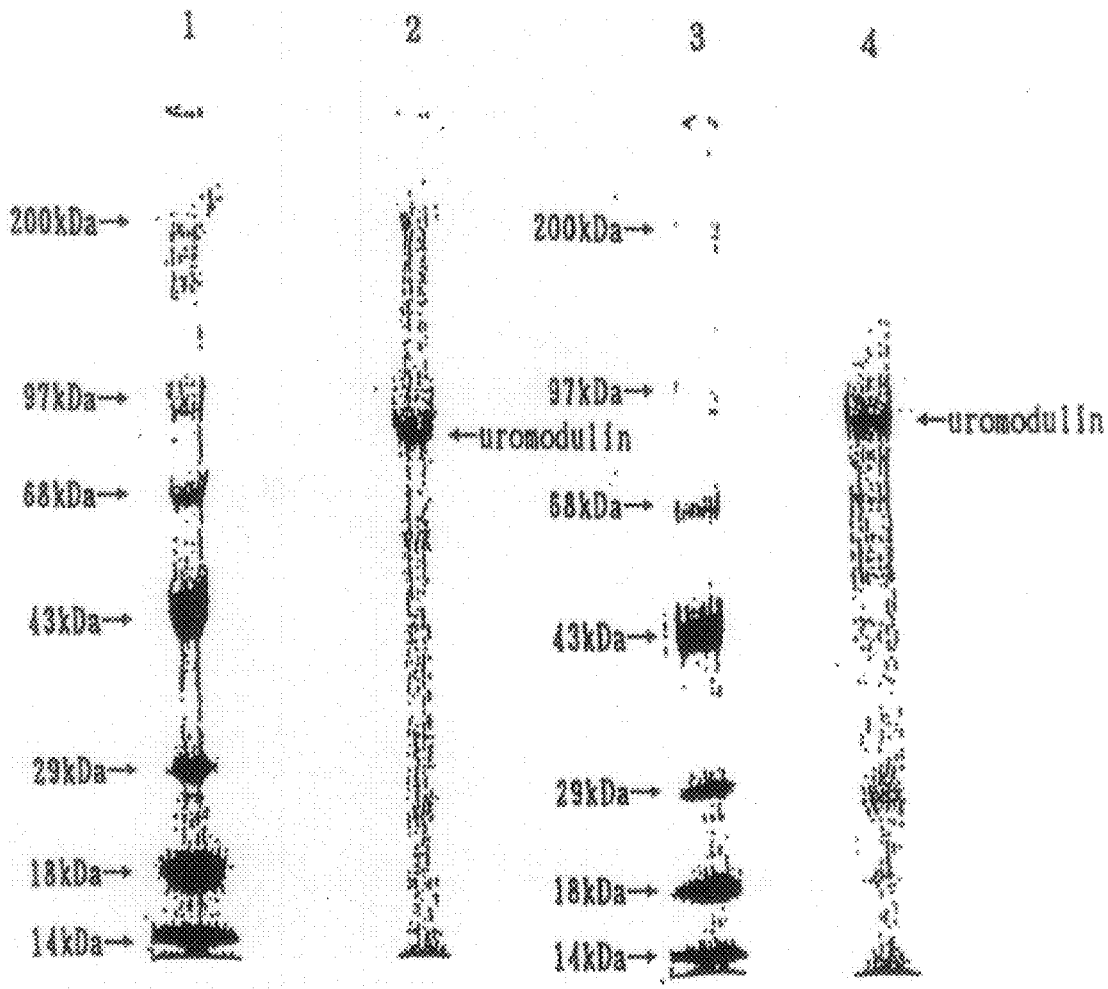
FIG. 4 is a photograph showing the electrophoretic patterns obtained when uromodulin as purified in Example 2 was subjected to SDS-PAGE individually under the reducing and non-reducing conditions.

Urine of pregnant women (in the second and a half month to sixth month of pregnancy) was admixed with sodium benzoate at a ratio of 2% against the volume of urine, followed by stirring for dissolution. The solution was adjusted to a pH of 3.9 with 16% hydrochloric acid and stirred for 60 min, whereby the resultant protein precipitate was allowed to be adsorbed efficiently on the finely pulverized precipitate of benzoic acid. The resultant aggregated precipitate was collected, washed with a 20-fold volume of cold saturated benzoic acid solution (0.3% (w/v)), and filter-pressed to separate out the precipitate. After the precipitate was admixed with a 3-fold volume of cold ethanol, the resultant solution was adjusted to pH 5.5 with 22% aqueous ammonia, then stirred for 30 min and left on standing at 4° C. for 3 hours, and two thirds of the supernatant were discarded. The remaining precipitate solution was added to Celite (diatomaceous earth) precoat (the trademark of Gemlite Super M (diatomaceous earth), produced by Shiroyama Kogyo K.K. of Japan), followed by filtration, and the precipitate was recovered ant stored at −30° C. The filtered wet cake was dissolved in PBS and dialyzed against PBS, and the dialysate was centrifuged at 15,000 rpm for 10 min and subjected to gel permeation by use of HPLC equilibrated with PBS (TSK3000-SW: produced by Tosoh Inc.of Japan) (see FIG. 3). The fractions which were eluted in the void volume were subjected to SDS-PAGE to determine the molecular weight and degree of purity (see FIG. 4). The fractions mainly containing uromodulin were collected and then passed through a 0.22 μm-filter, followed by storage at 4° C. Normal human urine was also able to be purified by the above-mentioned procedure.

EXAMPLE 3

Figure 5:
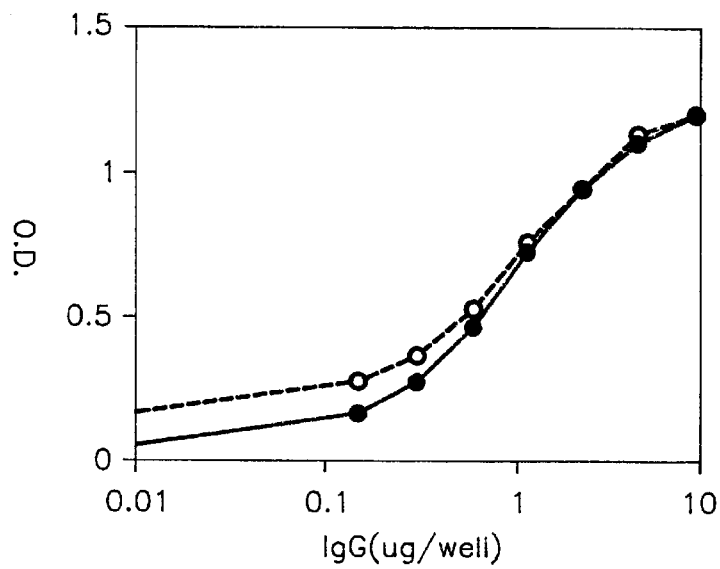
in FIGS. 5 (a) and (b), the symbols "◯" and "●" designate THG and uromodulin, respectively.
Figure 5:
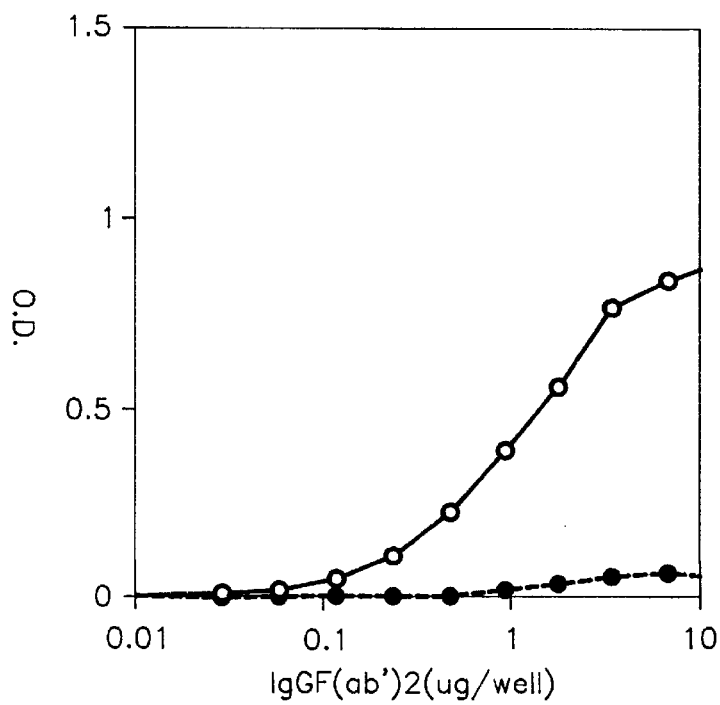

The purified THG and uromodulin as obtained in Examples 1 and 2 were diluted with 50 mM sodium carbonate buffer (hereinafter referred to briefly as "SCB", produced by Sigma Co. of U.S.A.) (pH 9.6), respectively, Each of the solutions was distributed in 50 μl portion into individual wells of a 98-wells plate (produced by Nunc Co.), followed by standing overnight at 4° C. The plate was washed with SCB, and 1% BSA-SCB solution was poured in 300 μl portion into each well, followed by standing overnight at 4° C. After the plate was washed with 20 mM Tris-buffered saline +0.05% Tween 20 (hereinafter referred to briefly as "TTBS") (pH 7.4), 2-fold serial dilutions of IgG (produced by Kappel Co.) with 1% BSA-TTBS starting with 3 mg/ml were poured in 50 μl portion into each well, followed by standing overnight at 40° C. to allow the reaction to proceed. After washing with TTBS, a 3000-fold dilution of peroxidase-labeled EIA-grade Protein C (produced by Biorad Co. of U.S.A.) was poured in 50 μl portion into each well, followed by reaction at 37° C. for 2 hours. After washing with TTBS and rinsing with SCB, coloring reaction was carried out with use of TMB peroxidase EIA Substrate Kit (produced by Biorad Co. of U.S.A.), followed by measurement of the absorbance at a wavelength of 450 nm with Plate Reader. As illustrated in FIG. 5 (a), it was found that THG and uromodulin react with human immunoglobulin IgG in a dose-dependent manner.

EXAMPLE 4

Each of the purified THG and uromodulin as obtained in Examples 1 and 2 was diluted with 50 mM SCB and distributed in 50 μl portion into individual wells of a 96-wells plate, followed by standing overnight at 4° C. After the plate was washed with SCB, 1% BSA-SCB solution was added in 300 μl portion to each well, followed by standing overnight at 4° C. After washing with TTBS, 2-fold serial dilutions of F(ab')$_2$ fragment of peroxidase-labeled human IgG (produced by Rockland Co. of U.S.A.) with 1% BSA-TTBS starting 3 mg/ml were poured in 50 μl portion into each well, followed by standing overnight at 4° C. After washing with TTBS and rinsing with SCB, the reaction was carried out with TMB peroxidase EIA Substrate Kit and measurement was taken of the absorbance at a wavelength of 450 nm. As illustrated in FIG. 5 (b), it was found that THG reacts with the F(ab')$_2$ fragment of human IgG in a dose-dependent manner, whereas uromodulin does not react readily with it.

EXAMPLE 5

With human urine and pregnancy urine being used as a specimen, each of the specimens was diluted with 50 mM SCB and distributed in 50 μl portion into individual wells of a 96-wells plate, followed by standing overnight at 4° C. After the plate was washed with SCB, 1% BSA-SCB solution was poured in 300 μl portion into each well. After washing with 20 mM TTBS, 2-fold serial dilutions of human IgG with 1% BSA-TTBS starting with 3 mg/ml were poured in 50 μl portion into individual wells, followed by standing overnight at 4° C. to allow the reaction to proceed. After washing with TTBS, a 3,000-fold dilution of peroxidase-labeled EIA-grade protein C was poured in 50 μl portion into each well, followed by reaction at 37° C. for 2 hours. After washing with TTBS and rinsing with SCB, the coloring reaction was conducted with TMB peroxidase EIA Substrate Kit, and measurement was taken of the absorbance at a wavelength of 450 nm with Plate Reader, with the result that there was obtained a finding comparable to the one of Example 3.

EXAMPLE 5

With human urine and pregnancy urine being used as a specimen, each of the specimens was diluted with 50 mM SCB and distributed in 50 μl portion into individual wells of a 96-wells plate, followed by standing overnight at 4° C. After the plate was washed with SCB, 1% BSA-SCB solution was poured in 300 μl portion into individual wells, followed by standing overnight at 4° C. After washing with 20 mM TTBS, 2-fold serial dilutions of human IgG with 1% BSA-TTBS starting with 3 mg/ml were poured in 50 μl portion into each well, followed by standing overnight at 4° C. to allow the reaction to proceed. After washing with TTBS, a 3,000-fold dilution of peroxidase-labeled EIA-grade protein C with 1% BSA-TTBS was further added in 50 μl portion to each well, followed by reaction at 37° C. for 2 hours. After washing with TTBS and rinsing with SCB, the coloring reaction was carried out with TMB peroxidase EIA Substrate Kit, and measurement was taken of the absorbance at a wavelength of 450 nm, with the result that there was obtained a finding comparable to the one in Example 3.

EXAMPLE 6

With human urine and pregnancy urine being used as a specimen, each of the specimens was diluted with 50 mM SCB and distributed in 50 μl portion into individual wells of a 96-wells plate, followed by standing overnight at 4° C. After the plate was washed with SCB, 1% BSA-SCB solution was poured in 300 μl portion into individual wells, followed by standing overnight at 4° C. After washing with 20 mM TTBS, 2-fold serial dilutions of the F(ab')$_2$ fragment of peroxidase-labeled human IgG starting with 3 mg/ml were poured in 50 μl portion into each well, followed by standing overnight at 4° C. to allow the reaction to proceed. After washing with TTBS and rinsing with SCB, the coloring reaction was carried out with TMB peroxidase EIA Substrate Kit and measurement was taken of the absorbance at a wavelength of 450 nm, with the result that there was obtained a finding comparable to the one in Example 4.

What is claimed is:

1. A process for purifying a protein and identifying the purified protein as Tamm-Horsfall glycoprotein or uromodulin which comprises the steps:

freezing human urine;

thawing the frozen urine to allow a precipitate to settle in a resulting solution, separating out the precipitate from the solution by centrifugation;

recovering by filtration the centrifuged precipitate;

dissolving the recovered precipitate in a phosphate-buffered saline solution;

dialysis of the dissolved precipitate against phosphate buffer saline effecting a dialyzate;

centrifuging the dialyzate to effect a supernatant;

separating out the supernatant, followed by concentration of the supernatant to effect a concentrate;

subjecting the concentrate to high performance liquid chromatography to isolate the protein-containing fraction;

subjecting the protein-containing fraction to gel permeation to effect purified protein; and identifying said purified protein by contacting the purified protein with anti-Tamm-Horsfall glycoprotein antibody, whereupon, interaction with said antibody identifies the purified protein as Tamm-Horsfall glycoprotein and no interaction with said antibody identifies said purified protein as uromodulin.

2. The process of claim 1, wherein the human urine is taken from men or non-pregnant women.

3. The process of claim 1, wherein the human urine is taken from pregnant women.

4. A process for purifying Tamm-Horsfall glycoprotein or uromodulin which comprises the steps:

dissolving sodium or ammonium benzoate in human urine;

acidifying the resultant benzoate solution sufficiently to allow absorption of a protein component in the urine on benzoic acid generated in the form of fine-powder aggregated precipitate;

separating out the protein component adsorbed on benzoic acid from the aggregated precipitate, followed by removal of the benzoic acid to effect a precipitate fraction;

dissolving the precipitate fraction in ethanol effecting a protein-containing solution;

adjusting the protein-containing solution to a pH value of 5.5, followed by treatment with diatomaceous earth and filtration to effect a separated protein-containing precipitate;

storing the separated precipitate at −30° C. and thereafter dissolving the stored precipitate in ethanol to thereby effect dialyzate; and centrifuging the dialyzate, followed by gel permeation to effect purified Tamm-Horsfall glycoprotein or uromodulin wherein the finally purified protein is identified as Tamm-Horsfall glycoprotein or uromodulin, depending upon whether or not said protein exhibits interaction with the $(Fab')_2$ fragment of IgG against Tamm-Horsfall glycoprotein.

5. The process of claim 4, wherein the human urine is taken from men or non-pregnant women.

6. The process of claim 4, wherein the human urine is taken from pregnant women.

* * * * *